(12) United States Patent
Parikh et al.

(10) Patent No.: US 11,299,702 B2
(45) Date of Patent: Apr. 12, 2022

(54) PORTABLE DISPOSABLE RE-USABLE CULTURE DEVICE FOR RAPID DIAGNOSIS OF INFECTIOUS AGENTS

(71) Applicant: Vax-Immune, LLC, Houston, TX (US)

(72) Inventors: Bhairavi Parikh, Palo Alto, CA (US); James Stone, Saratoga, CA (US)

(73) Assignee: Vax-Immune, LLC, Houston, TX (US)

(*) Notice: Subject to any disclaimer, the term of this patent is extended or adjusted under 35 U.S.C. 154(b) by 221 days.

(21) Appl. No.: 16/004,590

(22) Filed: Jun. 11, 2018

(65) Prior Publication Data

US 2018/0291327 A1 Oct. 11, 2018

Related U.S. Application Data

(63) Continuation-in-part of application No. 15/234,097, filed on Aug. 11, 2016, now Pat. No. 9,994,808, which is a continuation-in-part of application No. 15/131,338, filed on Apr. 18, 2016.

(60) Provisional application No. 62/270,754, filed on Dec. 22, 2015, provisional application No. 62/148,943, filed on Apr. 17, 2015.

(51) Int. Cl.
| | |
|---|---|
| *C12M 1/34* | (2006.01) |
| *C12M 1/00* | (2006.01) |
| *C12M 3/00* | (2006.01) |
| *C12M 1/02* | (2006.01) |
| *C12M 1/30* | (2006.01) |

(52) U.S. Cl.
CPC ............ *C12M 41/14* (2013.01); *C12M 1/005* (2013.01); *C12M 1/02* (2013.01); *C12M 1/30* (2013.01); *C12M 23/48* (2013.01); *C12M 23/50* (2013.01); *C12M 33/02* (2013.01)

(58) Field of Classification Search
CPC .......... C12M 1/005; C12M 1/02; C12M 1/30; C12M 23/48; C12M 23/50; C12M 33/02; C12M 41/14
See application file for complete search history.

(56) References Cited

U.S. PATENT DOCUMENTS

| | | | |
|---|---|---|---|
| 4,184,483 A | 1/1980 | Greenspan | |
| 7,955,841 B2 * | 6/2011 | Belgrader | ............... C12P 19/34 435/303.1 |
| 9,360,398 B2 | 6/2016 | Gold et al. | |
| 2003/0143752 A1 | 7/2003 | Feldsine et al. | |
| 2004/0014237 A1 | 1/2004 | Sugiyama et al. | |
| 2006/0205066 A1 | 9/2006 | Yum | |

(Continued)

FOREIGN PATENT DOCUMENTS

| | | |
|---|---|---|
| CN | 103765193 | 4/2014 |
| WO | WO2012177150 | 12/2012 |

(Continued)

OTHER PUBLICATIONS

Indian Office Action for Application No. 201717033146, dated Mar. 6, 2020.

(Continued)

*Primary Examiner* — Lydia Edwards
(74) *Attorney, Agent, or Firm* — Remenick PLLC

(57) ABSTRACT

The present invention is directed to compositions, tools, methods and devices to culture microorganisms and, in particular, to compositions, tools, methods and devices for the detection of microorganisms in biological samples.

30 Claims, 10 Drawing Sheets

(56) References Cited

U.S. PATENT DOCUMENTS

| | | |
|---|---|---|
| 2008/0261229 A1 | 10/2008 | Oppedahl et al. |
| 2009/0061450 A1 | 3/2009 | Hunter |
| 2010/0323392 A1 | 12/2010 | Yang et al. |
| 2012/0149603 A1* | 6/2012 | Cooney ............... B01L 3/50855 506/39 |
| 2013/0029324 A1* | 1/2013 | Rajagopal ............... B01L 3/502 435/6.1 |
| 2013/0236883 A1 | 9/2013 | Attache et al. |
| 2014/0072960 A1* | 3/2014 | Lansing ............. G01N 33/5302 435/5 |
| 2014/0152459 A1 | 6/2014 | Olson et al. |
| 2014/0234949 A1* | 8/2014 | Wasson ............ G01N 35/00871 435/287.2 |
| 2014/0255984 A1 | 9/2014 | Sharpin |

FOREIGN PATENT DOCUMENTS

| | | |
|---|---|---|
| WO | 2014/152459 | 9/2014 |
| WO | WO2014152459 | 9/2014 |
| WO | WO 2014152459 A1 | 9/2014 |

OTHER PUBLICATIONS

Chinese Office Action for CN App. No. 201680022323.8, dated Mar. 19, 2020.
EPO Search Report of EP App. No. 16780986, dated Apr. 9, 2020.
Chinese Office Action for CN App. No. 201680022323.8, dated Dec. 4, 2020.
Michael Hogardt et al., "Specific and Rapid Detection by Fluorescent In Situ Hybridization of Bacteria in Clinical Samples Obtained from Cystic Fibrosis Patients," Journal of Clinical Microbiology vol. 38(2): pp. 818-825, Feb. 2000.
Sarah E. Gilbert et al., "Evaluation of Swabs and Transport Media for Recovery of Yersinia Pestis," Journal of Microbiological Methods vol. 96: 35-41 (2014).
Chinese Office Action for CN App. No. 201680022323.8, dated Apr. 7, 2021.

* cited by examiner

PORTABLE DISPOSABLE RE-USABLE CULTURE DEVICE FOR RAPID DIAGNOSIS OF INFECTIOUS AGENTS

REFERENCE TO RELATED APPLICATIONS

This application is a Continuation-In-Part Application of U.S. Non-Provisional application Ser. No. 15/234,097, filed Aug. 11, 2016, which is a Continuation-In-Part Application of U.S. Non-Provisional application Ser. No. 15/131,338, filed Apr. 18, 2016, which claims priority to U.S. Provisional Application Nos. 62/148,943, filed Apr. 17, 2015, and 62/270,754, filed Dec. 22, 2015, all entitled "Portable Disposable Re-Usable Culture Device for Rapid Diagnosis of Infectious Agents," and all hereby specifically and entirely incorporated by reference.

BACKGROUND

1. Field of the Invention

The present invention is directed to compositions, tool, methods and devices to culture microorganisms and, in particular, to compositions, tools, methods and devices for the detection of microorganisms in biological samples.

2. Description of the Background

Microorganisms such as bacteria, virus, parasites and more can be life-threatening infections when detected in a patient. Often, the ability to save a life depends on the prompt identification of the infectious agent so that appropriate antimicrobial therapy can begin. Certain infections can be detected and identified directly from an analysis of a biological sample, whereas others require culturing of the sample to increase the number of microorganisms to a detectable level. With regard to the later, incubators have proven to be an invaluable tool. Very simply, the biological sample is placed in an incubator and allowed to proliferate under conditions that promote growth. After a period of time the microorganism, if present, becomes detectable.

Many different incubators have been developed and are available commercially (e.g., see U.S. Pat. No. 3,796,639). The key features of an incubator include the ability to properly culture the sample and to maintain containment of the sample. A need exists to reduce the time between collection of samples from a patient or source and identification of the infection so that administration of the correct antimicrobial therapy can either begin or be avoided.

SUMMARY OF THE INVENTION

The present invention overcomes the problems and disadvantages associated with current strategies and designs and provides new tools, compositions, methods and devices for culturing and detecting microorganisms.

One embodiment of the invention is directed to a disposable and/or reusable kit for detection of a microorganism or group of microorganisms in a biological sample. The kit comprises a culture device comprising an incubator and an environmental chamber into which is placed the incubator or the incubator is attached, culture medium contained within the incubator that promotes the proliferation or stabilization of the microorganism or group of microorganisms, and a collection tool for obtaining the biological sample and directing delivery of the biological sample to the incubator. In a preferred embodiment, the collection tool is a flocked swab. Preferably, the culture medium comprises one or more ingredients which promote the proliferation or stabilization of the microorganism or group of microorganisms. The culture medium preferably comprises ingredients that inhibit proliferation or stabilization of one or more microorganisms that are not the microorganism or group of microorganisms to be detected. Preferably, environmental chamber contains one or more devices that control the environment of the incubator. In a preferred embodiment, the one or more devices comprise a heating element, a cooling element, a pH control element, a humidity control element, an oxygen control element, a carbon dioxide control element, a vibrator, or a light control element. Preferably, the environmental chamber contains a USB port that connects the one or more devices to an external processer containing software that controls the operation of the one or more elements, or the environmental chamber contains a microprocessor that contains software to control the one or more environmental control elements.

Preferably the culture device is comprised of plastic. In a preferred embodiment, the culture device further comprises a micro-fluidic device, wherein the micro-fluidic device allows for inclusion of a lateral flow assay or device incorporated into the incubator for testing the biological sample upon completion of incubation with or without an optical reader to read or report a result.

Another embodiment of the invention is directed to a method of detecting a microorganism or group of microorganisms. The method comprises the steps of obtaining a biological sample with or without a collection tool, placing the biological sample into an incubator containing culture medium for the proliferation and or stabilization of the microorganism, sealing the incubator closed, placing the closed incubator within or attached to an environmental chamber, allowing the microorganism or group of microorganisms to proliferate and or stabilize in the incubator for a period of time, and assessing proliferation and or stabilization of the microorganism or group of mircoorganisms to determine the presence or absence of the microorganism or group of microorganisms in the biological sample.

Preferably, the biological sample is self-obtained. In a preferred embodiment, the environmental chamber contains one or more environmental control elements. Preferably, the one or more environmental control elements comprise a heating element, a cooling element, a pH control element, a humidity control element, an oxygen control element, a carbon dioxide control element, a vibrator, or a light control element. Preferably, the environmental chamber contains a USB port that connects the one or more environmental control elements to an external processer containing software that controls the operation of the one or more environmental control elements and/or the environmental chamber contains a microprocessor that contains software to control the one or more environmental control elements. The method preferably further comprises determining a quantitative or relative concentration of the microorganism or group of microorganisms.

In a preferred embodiment, the period of time is from 1 hour to 7 days. Preferably, assessing comprising removing a sample from inside the incubator and determining the presence or absence of the microorganism. Preferably, assessing comprising performing a visual or chemical assessment, immunoassay, lateral flow assay, enzyme linked immunoassay, an immunochemistry assay, a polymerase chain reaction, a latex agglutination, other microbiologic assay or a combination thereof. In a preferred embodiment, assessing comprising insertion of a device to perform an analysis. The analysis preferably comprises a visual analysis, a chemical analysis, an immunoassay, a lateral flow assay, an enzyme linked immunoassay, an immunochemistry assay, a polymerase chain reaction, a latex agglutination, other microbiologic assay or a combination thereof.

Preferably, the analysis is a visual analysis and the method further comprises determining at least one of turbidity and color change with an optical reader. The method preferably further comprises transmitting the assessment electronically to a physician, health care worker, a professional, an expert, a patient or another individual, or to a patient's medical or health care record. Preferably, the transmitting is accomplished by a WiFi.

Another embodiment of the invention is directed to an incubator. The incubator comprises a base, a lid adapted to be coupled to the base, a sample gathering device coupled to the lid, a multi-chamber cavity within the base, and a seal adapted to prevent fluid from escaping a first chamber of the multi-chamber cavity and entering a second chamber of the multi-chamber cavity.

Preferably, the sample gathering device is a flocked swab. In a preferred embodiment, the flocked swab is coupled to the lid by a rod. The incubator preferable further comprises a sample conditioning device. Preferably, the sample conditioning device is one of a fluid agitator, a heating device, a cooling device, a moisture removal device, a moisture adding device, a pH control element, a humidity control element, an oxygen control element, a carbon dioxide control element, or a light control element. In a preferred embodiment, the sample conditioning device is housed in a third chamber of the multi-chamber cavity and the third chamber is sealed from the first and second chambers.

Preferably, the incubator further comprises a switch adapted to activate the sample conditioning device. Preferably, the seal is a penetrable membrane adapted to be pierced by the sample gathering device. In a preferred embodiment the base and the lid are maintained in a first position prior to sample gathering and are maintained in a second position after sample gathering. Preferably, in the first position the swab is maintained outside the first chamber and in the second position the swab is maintained within the first chamber.

Another embodiment of the invention is directed to a sample evaluation system. The system comprises an incubator comprising: a base, a lid adapted to be coupled to the base, a sample gathering device coupled to the lid, a multi-chamber cavity within the base, and a seal adapted to prevent fluid from escaping a first chamber of the multi-chamber cavity and entering a second chamber of the multi-chamber cavity; and a sample conditioning fluid housed within the first chamber.

In a preferred embodiment, the sample gathering device is a flocked swab. Preferably, the flocked swab is coupled to the lid by a rod. The incubator preferably further comprises a sample conditioning device. Preferably, the sample conditioning device is one of a fluid agitator, a heating device, a cooling device, a moisture removal device, a moisture adding device, a pH control element, a humidity control element, an oxygen control element, a carbon dioxide control element, or a light control element. The sample conditioning device is preferably housed in a third chamber of the multi-chamber cavity and the third chamber is sealed from the first and second chambers. Preferably, the incubator further comprises a switch adapted to activate the sample conditioning device. Preferably, the seal is a penetrable membrane adapted to be pierced by the sample gathering device.

Preferably, the base and the lid are maintained in a first position prior to sample gathering and are maintained in a second position after sample gathering. In a preferred embodiment, in the first position, the swab is maintained outside the first chamber and, in the second position, the swab is maintained within the first chamber so that the sample comes into contact with the sample conditioning fluid. Preferably, the sample is a microorganism or group of microorganisms and the sample conditioning fluid is a culture medium that promotes the proliferation or stabilization of the microorganism or group of microorganisms.

Another embodiment of the invention is directed to an incubator. The incubator comprises a base and a sample assembly contained within the base. The sample assembly comprises a lid, a sample gathering device coupled to the lid, and an ampule. The sample assembly is positionable between a sample gathering position and a sample incubating position.

Preferably, the sample gathering device is a flocked swab. The flocked swab is preferably coupled to the lid by a rod. In a preferred embodiment, the incubator further comprises a sample conditioning device. Preferably, the sample conditioning device is one of a fluid agitator, a heating device, a cooling device, a moisture removal device, a moisture adding device, a pH control element, a humidity control element, an oxygen control element, a carbon dioxide control element, or a light control element.

In a preferred embedment, the sample gathering device is maintained outside the ampule in the sample gathering position and is forced into the ampule in the sample incubating position. The incubator preferably further comprises a penetrable membrane separating contents of the ampule from the sample gathering device, wherein the penetrable membrane adapted to be pierced by the sample gathering device. The incubator preferably further comprises a switch adapted to activate the sample conditioning device. Preferably, the incubator is adapted to collect, process, transport, and stabilize a sample for use in biomarker determinations or cancer tissue testing. The incubator is preferably adapted to collect, incubate, and transport a biological sample.

Another embodiment of the invention is directed to a sample evaluation system. The system comprises an incubator comprising a base and a sample assembly contained within the base, and a sample conditioning medium housed within an ampule. The sample assembly comprises a lid, a sample gathering device coupled to the lid and the ampule. The sample assembly is positionable between a sample gathering position and a sample incubating position.

Preferably, the sample gathering device is a flocked swab. In a preferred embodiment, the flocked swab is coupled to the lid by a rod. Preferably, the incubator further comprises a sample conditioning device. The sample conditioning device is preferably one of a fluid agitator, a heating device, a cooling device, a moisture removal device, a moisture adding device, a pH control element, a humidity control element, an oxygen control element, a carbon dioxide control element, or a light control element. Preferably, the sample gathering device is maintained outside the ampule in the sample gathering position and is forced into the ampule in the sample incubating position. The system preferably further comprises a penetrable membrane separating contents of the ampule from the sample gathering device, wherein the penetrable membrane adapted to be pierced by the sample gathering device.

The system preferably further comprises a switch adapted to activate the sample conditioning device. Preferably, the sample is a microorganism or group of microorganisms and the sample conditioning fluid is a culture medium that promotes the proliferation or stabilization of the microorganism or group of microorganisms. The incubator is preferably adapted to collect, process, transport, and stabilize the sample for use in biomarker determinations or cancer tissue testing.

Other embodiments and advantages of the invention are set forth in part in the description, which follows, and in part, may be obvious from this description, or may be learned from the practice of the invention.

DESCRIPTION OF THE INVENTION

Figure 1:
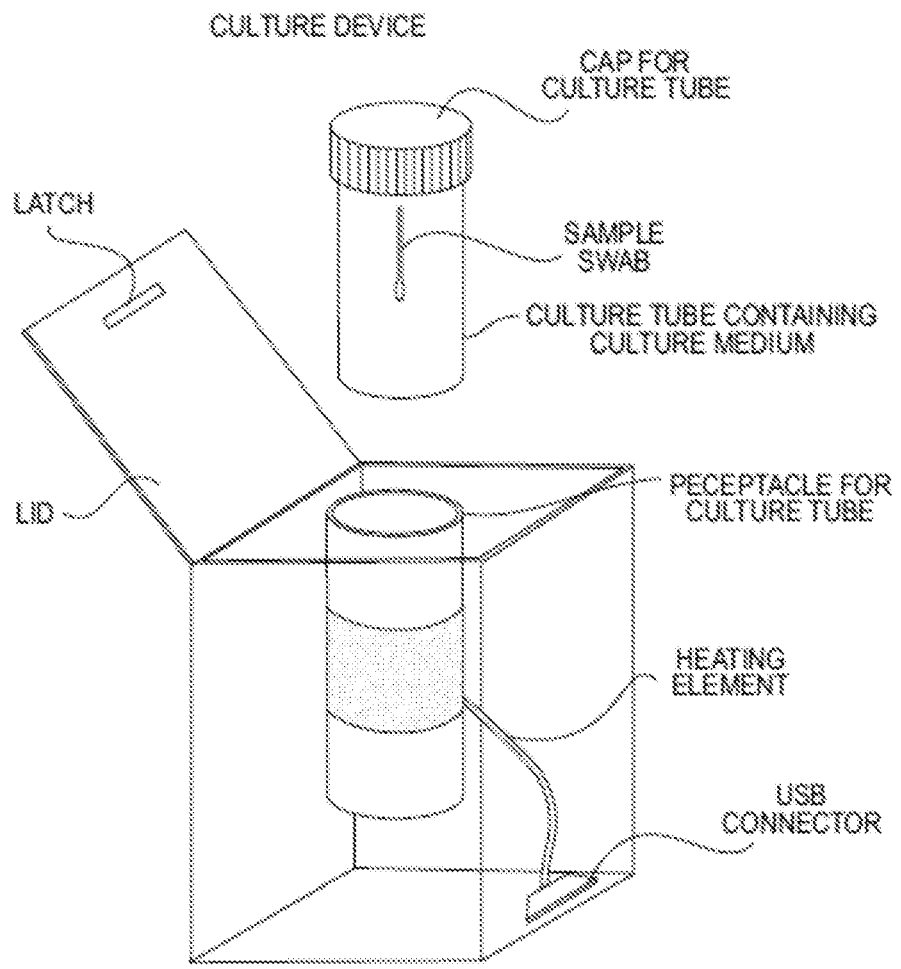
FIG. 1 One embodiment of the device of the invention.
Figure 2A:
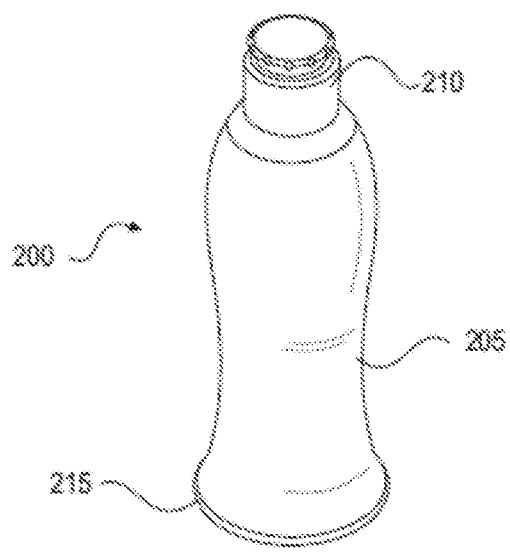
FIGS. 2A-D Views of one embodiment of an incubator of the invention.
Figure 2B:
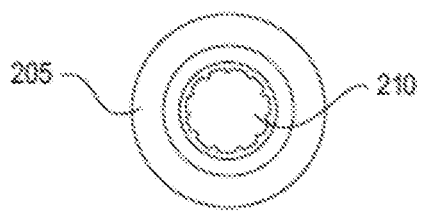
Figure 2C:
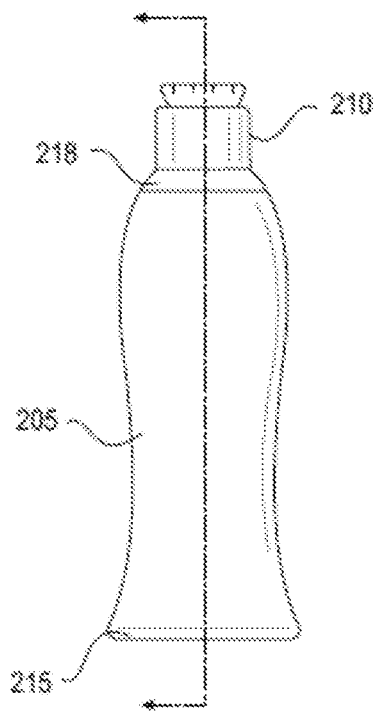
Figure 2D:
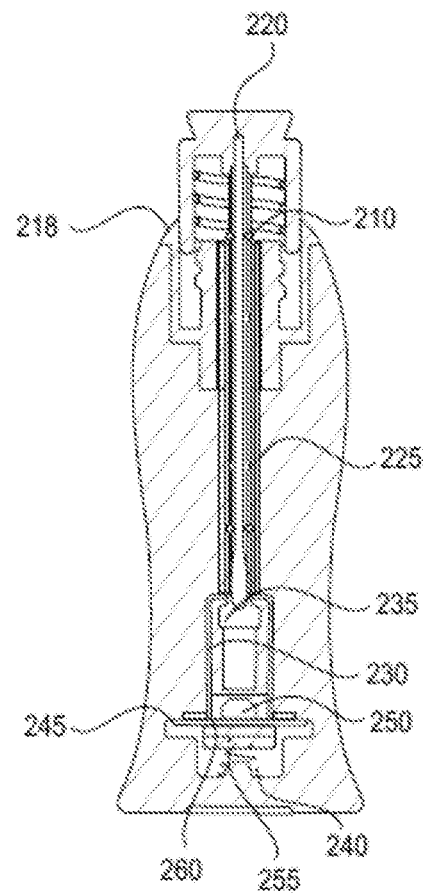

Culture devices are well known and commercially available in many different forms. Culture devices are configured to control and maintain a suitable environment for the proliferation of desired organisms followed by subsequent analysis and detection. Culture devices are typically bulky, expensive to build, complicated to operate; requiring personnel with specialized training, and require cleaning followed by sterilization before re-use.

Culture devices as disclosed herein have been developed that are portable, inexpensive to build and operate, as compared to conventional devices, and disposable. Culture devices of the invention are adapted to transport samples and comprise a disposable and optionally hand-held incubator containing growth medium, into which is placed a biological sample, and an environmental chamber which may be re-usable into which is placed the incubator or the incubator is fixed into the environmental chamber. Preferably the incubator, which is disposable, is a container that comprises growth medium that encourages the growth of the microorganism and/or host organisms which is required for proliferation or stabilization of the microorganism of interest. Preferably, the device preserves the sample. For example, the device may contain a medium that prevents the sample from decomposing, breaking down, oxidizing, or otherwise degrading. The container may be any geometric shape such as, for example, a cube or preferably a cylinder. The environmental chamber, which may be disposable or reusable, controls and/or maintains the environmental conditions of the incubator necessary for the growth and propagation and or stabilization of a specified microorganism or group of microorganisms. Devices of the invention can be designed to promote the growth and or stabilization of one or more specific microorganisms or classes of microorganisms including, for example, bacteria, viruses, fungi, parasites and/or other infectious agents (collectively "microorganisms"). The culture devices of the invention provide and maintain temperatures within a range required for optimum growth and or stabilization of the specified microorganism or group of microorganism and/or for optimum growth and or stabilization of host organisms such as cells or other host organisms that are infected with the microorganism or group of microorganisms to be detected. The unique design and composition of the device permits use by trained professionals and by persons with minimum or no training and can include instructions for operation by lay persons such as the patient. The device allows for the easy collection of a biological sample in a sterile, semi-sterile, or non-sterile fashion which is easily and securely placed into an incubator portion, containing growth media and securely closed. In other embodiments, the sample may be a non-microbial or non-biological sample. The incubator is placed into an environmental control chamber or may be already fixed into the environmental control chamber that may include heating and/or cooling elements, pH control element, oxygen control element, carbon dioxide control element, fluid agitation element, ambient temperature monitor element, light control element, and/or a desired humidity control element. The device can be connected through a USB or other information transfer circuit to be maintained and/or controlled through a processor and/or the environmental chamber contains a microprocessor that contains software to control the one or more environmental control elements. The processor is pre-programmed to operate the environmental chamber under predetermined conditions of, for example, temperatures, humidity, pH, oxygen concentration or other environmental parameter. The device of the invention operates independently for a period of time and without any need for further maintenance, whether constant or occasional. After a pre-specified period of time, as determined by the microorganism or group of microorganisms to be detected and preferably at ambient temperatures, the entire device is either brought to a physician, a health care worker, a professional or other expert with regard to the analysis to be performed, to determine the presence of absence of the microorganism in the biological sample or tested by the patient, and in either case, the results may be transmitted to the physician, health care worker, a professional or other expert or the hospital or clinic medical record of the patient electronically. For example, the results may be transmitted by wired or wireless (e.g. WiFi, Bluetooth) communication protocols.

In other embodiments, a purchaser of the culture device may be able to scan a barcode or QR code (for example, QR code 770 in FIG. 7A), take a picture of the device, or otherwise sync the culture device to their smartphone, tablet, or computer. For example, a purchaser may use their smartphone to scan a QR code on the culture device's label. Preferably, each culture device has a unique QR code. Once scanned, the phone may direct the purchaser to download a software application ("app") that is able to interface with the culture device. The app will preferably then sync with the culture device. The app may provide instructions (e.g. written, audible, or visual) on how to use the culture device to obtain a sample. The app may also communicate with the culture device by wired or wireless (e.g. WiFi, Bluetooth) communication to monitor the incubation of the sample and provide a result to the purchaser. For example, once the incubation is complete the app may alert the purchaser if they have or do not have the virus that the culture device is testing for. The app may also alert the purchaser if there is a problem with the incubation or the sample is insufficient.

One embodiment of the devices of the invention comprises an environmental chamber containing an incubator in the form of a receptacle of a size that preferably is between about 0.5 ml and about 10 ml of volume, more preferably from about 1-5 ml, and more preferably from about 1-3 ml. The receptacle size may be any three-dimensional geometric structure such as a cube, a tube or cylinder. The receptacle is designed so as to promote the ease of administration or inoculation of a sample such as, for example, a biological, agricultural or environmental sample. Preferably the container is the minimum volume necessary to promote growth of the microorganism to detectable levels. An inoculation tool may comprise, for example, a swab, a stick, a brush, a cotton ball, a sponge, a needle, a pipette or another sample collection mechanism that allows for collection of the sample or direct administration of the sample (e.g. oral secretions or spit) suspected of containing the microorganism to be detected. Preferably, the collection tool is a flocked swab.

A preferred biological sample is a sample that can be obtained by a person without assistance. The person can be a patient, a patient's helper, a medical professional, a layperson, or another person. Preferably the person is without professional training in the art of this sample collection. For example, preferred samples are swabs obtained from the mouth (e.g., oral cavity, throat), nasal passages, eyes, ears, mammary discharge, anus, vagina, cervix, urine, stool, skin, hair, finger stick blood or other means of obtaining blood, or finger or toe nails. Preferred environmental samples include samples obtained from soils, bodies or water, animals, foodstuffs, and any biomass.

The device of the invention is useful for the detection of microorganisms and preferable viruses such as, for example, influenza virus, adenovirus, coronavirus, rhinovirus, enteric viruses, herpes virus, papilloma viruses, rotavirus, vesicular viruses, or many other viruses, bacteria such as, for example, mycobacteria (e.g., *Mycobacterium tuberculosis*), *mycoplasma* (e.g. *Ureaplasma parvum, Ureaplasma urealyticum*), *salmonella, streptococcus, bacillus, pseudomonas* or many other bacteria, fungal microorganisms such as, for example, Cryptococci, *aspergillus* and *candida*, or many other fungal microorganisms, and/or parasites such as, for example, endoparasites, protozoan, and helminth, or many other parasite microorganisms.

The device of the invention may optionally contain an amount of a host organism necessary for proliferation and/or detection of the microorganism or group of microorganisms of interest. Host organisms include, for example, feeder layers of eukaryotic or prokaryotic cells, cells that produce growth factors that promote microorganism proliferation, stabilization, and/or inhibit proliferation of other microorganisms or organisms. Typical feeder layers comprise eukaryotic or prokaryotic cells for the detection of microorganisms of interest.

The device preferably contains a predetermined amount of a growth medium. Preferably, the container is a small cylinder with a volume of from 0.5-10 cc that holds from 0.5-10 ml of culture medium. However, the cylinder can have another volume, for example the cylinder may be able to hold up to 50 ml, up to 100 ml, or up to 250 ml, or larger.

Additionally, the cylinder may be a commonly used culture vial. Many different growth media are commercially available or can be prepared from the known growth requirements of a particular microorganism or group of microorganisms. The medium is preferably a fluid or a gel, and may be a solid, a liquid or a semi-solid material, selected to promote the growth and or stabilization of certain microorganism or group of microorganisms suspected to be within the sample and/or the host organisms. Also preferably, the medium contains ingredients that inhibit the growth of other microorganisms and/or organisms that do not enhance the detection or the microorganism or group of microorganisms of interest. Preferably, the medium allows for the concentration and preservation of the sample so that diagnostic procedures can be applied to diagnose the presence or absence of the specific microorganism or group of microorganisms after the incubation period. Preferably the media of the container allows for ease of placement of the sample via swab, needle, pipette or other inoculation tool or directly without a collection tool. Growth medium and conditions that permit proliferation of many microorganisms is well known and commercially available to those skilled in the art (e.g. see, LifeTechnologies, Grand Island, N.Y.; Medical Microbiology, 26th edition, Jawetz, Melnick, & Adelberg's Medical Microbiology; Clinical Microbiology, 11$^{th}$ edition Jorgensen and Pfaller's, Manual of Clinical Microbiology).

In some embodiments, the device is used for the collection, initial processing, transport, and temperature stabilization of samples for use in biomarker determinations or cancer tissue testing. Preferably the temperature stabilization includes incubation and heating or cooling to maintain a specific temperature. For example, the temperature may be ambient temperature (i.e. 20 to 30° C.), a refrigerated temperature (i.e. 2 to 8° C.), or a frozen temperature (i.e. at or less than 20° C.). The sample may be blood, body tissues, other body fluids, tumors, or another biological sample.

Also preferable, the container allows for ease of withdrawal of a sample after incubation to allow detection of the microorganism, for example, via a swab, needle or a pipette, and thereafter interface with a diagnostic device such as, for example, a lateral flow assay, ELISA, PCR, next-generation sequencing device, microarray analysis device, or like or combinations of these. In other embodiments, the diagnostic device may be insertable and removable from the container. For example, a PCR cassette may be inserted into the container prior to incubation and once incubation is complete, the PCR cassette may be removable and a user may be able to determine the results or the cassette may be further processed to determine the results. In other embodiments, the cassette may be built-in and non-removable. The results from the testing may be read by an optical reader within the container or another reader capable of determining the results of the test. Preferably the cassette is coupled to the sample vile by micro-fluidics. The diagnostic device may be powered by a power source within the container, self-powered, or not need power. Alternatively, the incubator does not require withdrawal of a sample after incubation but instead contains culture medium that also comprises a chemical that provides for visual or chemical detection of microorganism growth. The chemical may be a specific enzyme that reacts with a component, such as a specific biochemical, enzyme, or sequence (e.g., nucleic acid or amino acid) produced by the cultured microorganism. Alternatively, the incubator does not require withdrawal of a sample after incubation but instead connects directly to a device or allows insertion or incorporation of the device into the incubator to perform the analysis such as, for example immunoassay (e.g. a lateral flow assay, or an enzyme linked immunoassay, or an immunochemistry assay), a polymerase chain reaction assay, or a visual reading (e.g. when using chromogenic media by direct visualization of the media color or via optical reader) or microbiologic assay, or the like or a combination of these. One advantage of having a visual or chemical detection or direct connection to a device or insertion of the test into the device is that the container does not need to be opened and can be disposed of safely and securely without generating any additional biological waste.

Preferably the devices of the invention include a temperature control mechanism such as, for example, a heater or cooler that may be maintained at a set temperature and/or activated and/or deactivated by a sensor that provides temperature information regarding the interior of the container. Suitable temperature control devices are commercially available and include, but are not limited to probe heaters, temperature-control heaters, and coolers. Storage temperature can be preset on heaters or temperature-control devices, or contained in the media container that is inserted into the device or on a microchip contained in the device. Preferably, the device includes an internal temperature sensor in or on the incubator to monitor and adjust the incubator's temperature is maintained at the set levels.

Preferably, the container is designed to promote the ease of use of diagnostic assays that can be applied after growth of the specific microorganism or group of microorganisms. Suitable assays include, but are not limited to, visual or chemical assessment assays, immunoassays (e.g. a lateral flow assay, or an enzyme linked immunoassay, or an immunochemistry assay), a polymerase chain reaction assay, or microbiologic assay, or the like or a combination of these.

Samples to be introduced into the devices of the invention that are suspected to contain microorganisms to be cultured and detected may be obtained from sources where infectious agents are found. For example, biological samples may be obtained from humans or other animals, environmental samples may be obtained from the land or water, or other regions such as man-made waste sites and the like. Biological samples include, but are not limited to, respiratory including nasal, oral and tracheal, intestinal including gastric and stool, genitourinary including vaginal, cervical, prostate, and urine, skin including abscesses and wounds, and other body fluids including blood, cerebrospinal spinal fluid, peritoneal fluid, and pleural fluid, or other sources.

Preferably the devices of the invention are cultured for a period of time during which, no maintenance is required. Preferably, the period of time is about 14 days. However, the period of time can be less (i.e. 1 day, 3 days, 7 days, or 10 days) or more (i.e. 20 days, 30 days, or 60 days). The devise is either maintained independently or coupled to a control mechanism through, for example, a USB port. The USB port allows for an external processor to control one or more sensors and/or control elements placed within the environmental chamber to raise or lower the temperature, pH, humidity, light exposure, oxygen concentration, carbon dioxide concentration or another environmental parameter of the chamber and/or the incubator or environmental conditions outside the device (e.g. ambient temperature), and/or the environmental chamber contains a microprocessor that contains software to control the one or more environmental control elements. Additionally, the USB connection may allow the sample to be incubated for extended periods of time, for example 2 weeks, 4 weeks, 2 months, or 6 months by supplying external power to the device. In another embodiment, the device may be able to be plugged into a wall outlet to be powered. Preferable, the incubator can be maintained, either independently or under control of an automated system, for a period of time such as, for example, from 1 hour to 14 days, more preferable from 2 hours to 7 days, and more preferable from 4 hours to 3 days. Preferably, the incubator includes a timer (either a physical timer or a software based timer) that measures the incubation period and outputs a signal indicating the amount of time that the sample has been incubated. For example, the timer may use one light to indicate that the sample is being incubated and another light to indicate that the incubation is complete. The incubator may additionally have an optical reader. The optical reader may be adapted to determine turbidity in the fluids (for example, to determine if the sample has sufficiently been incubated) or color changes within the fluids (for example, to determine if specific bacteria is present, chromogenic media may be used).

The devices of the invention preferably are compatible with commercially available detection kits (e.g. those being developed by Vax-Immune for rapid diagnosis of various microorganisms or group of microorganisms), with an operating temperature that can be set for one or more temperatures and/or temperature ranges (e.g., about 35° F. to about 98° F. (2° C. to 37° C.). Preferably the device is powered via a USB connector, a battery, or an external power source (e.g., at 110/115 v or 220/240 v). Preferably the temperature set point is from 35° C. to 37° C. (+/−1° C. or 2° C.) for bacterial, fungal or viral growth, and 2° C. to 37° C. (+/−1° C. or 2° C.) for media storage with a microprocessor to monitor and control temperature and time. Also preferably the device is portable and of a size that fits in the palm of a hand with an on-off switch to engage for bacterial, viral, fungal or other microbial growth. The switch may be located on the lid or another location on or within the device.

The device of the invention provides a simplified collection device and incubator that can be hand carried from place to place. The portable device of the invention preferably comprises a chamber having an open top or side for receiving or contains a closed receptacle containing the biological sample and growth medium. A lid is clamped to the top of the chamber for closing the same, the chamber having a seal for engaging the lower surface of the lid near its outer periphery. Optionally, the chamber is fitted with a conduit in fluid communication with the exterior to carry one or more fluids or gases or other elements into and/or out of the chamber. The conduit may have terminal ends with valves for controlling the flow of fluid or gases or elements through the conduit.

The incubator can be placed into or is built into the chamber having a top or side wall provided with an opening for receiving the incubator. The chamber may have heating coils on one or more of its side or bottom walls or on one or more side or bottom walls of the incubator for heating the contents of the incubator. In an alternative embodiment, the chamber is a cylinder extending downwardly from the top wall for receiving or containing a cylindrical incubator, the cylinder being of heat conductive material and provided with a heater coil carried by and surrounding its outer surface. The latter embodiment provides better heat distribution within the incubator and eliminates any electrical shock hazards which might arise by a person inserting a hand into the housing. The portable incubator of the invention combines versatility, safety and economy with absolute integrity in culture or microorganism growth or sample stabilization.

Another embodiment of the invention is directed to a kit comprising a culture devise of the invention comprised of an incubator containing a desired culture medium, and an environmental chamber, in addition to a sample collection device, a sample withdrawal device and optionally a detection mechanism. Preferred sample collection and/or sample withdrawal devices include swabs, needles, pipettes and other inoculation and/or collection devices but in other options, samples can be placed directly into the chamber. Preferable, the sample collection device is designed to interact and deposit sample into the container with sterility or near sterility, in other words there is no contamination of the sample attributable to the collection or deposition of the sample into the device of the invention.

Another embodiment of the invention comprises methods of collection, incubating and detecting a microorganism or group of microorganisms of the sample. Preferable, sample is collected with a sample collection device that is designed to avoid contact with anything but the sample source and the culture container. The culture container contains media prepared to promote culturing of the microorganisms of interest and/or inhibit microorganisms of no interest. Also preferable the sample is incubated on or within the media after which, a sample is removed from the container for analysis or the analytic device is inserted into the container. Preferably the sample removed or tested is analyzed for the presence and/or absence and or concentration of the microorganism or group of microorganisms of interest such as, for example by, visual or chemical assessment, immunoassay (e.g. a lateral flow assay, or an enzyme linked immunoassay, or an immunochemistry assay, or a latex agglutination), a polymerase chain reaction, or the like or a combination of these. Alternatively, the incubator does not require withdrawal of a sample after incubation but instead connects directly to a device that performs the analysis such as, visual or chemical assessment, immunoassay (e.g. a lateral flow assay or an enzyme linked immunoassay, or an immunochemistry assay, or a latex agglutination), a polymerase chain reaction, other microbiologic assay, or the like or a combination of these.

After analysis by a physician, health care worker or other professional or expert in the microorganism of interest, or the patient or individual who collected the sample, the device can be safely disposed as biological waste. Preferably, no additional biological waste is generated during the analysis.

While the invention is described for use with obtaining, culturing, and analyzing microorganisms, the invention can be used for other sample taking of non-microbial or non-biological samples. For example, the device may be used for collecting DNA. The sample may be saliva or another bodily fluid or tissue (e.g. tumor sample) and the medium may be a substance used to prevent the breakdown of the DNA, etc. The sample may be a liquid biopsy sample, a tissue sample, a microbiome sample, or another biological sample. The device may be used for diagnosing conditions with the samples, testing for conditions of the samples, transporting and/or storing the samples, processing the samples, or otherwise treating the samples. As another example, the device may be used for testing water quality, soil composition, air quality, or other environmental considerations. The sample may be dirt, water, rocks, air or other substance and the medium may be a substance used to breakdown the sample.

The following examples illustrate embodiments of the invention, but should not be viewed as limiting the scope of the invention.

EXAMPLES

Example 1

One embodiment of the invention is depicted in FIG. 1. Shown is a cylindrical container enclosed within a square chamber. The square chamber holds a heating element wrapped about the cylinder and a USB connection connectable to a processor outside of the container. The processor contains software designed to control the heating and or cooling element and optionally the environment within the container (e.g., humidity, pH, UV or visible light, oxygen concentration, carbon dioxide concentration). Also shown is a capped cylindrical container that contains a culture medium designed to promote the proliferation and or stabilization of a desired microorganism or group of microorganisms. Also depicted is a sample collection device in the form of a swab embedded within the culture medium. The swab can be used to collect a sample from a desired biological source and the sample placed within or on top of the culture medium, as shown or a sample can be directly placed into the culture medium. The cap is then secured as depicted which provides sterile conditions for proliferation and or stabilization of microorganisms from the collection swab. The receptacle can be easily placed within the heated chamber and the chamber closed with a secure latch.

Example 2

Twenty women are tested conventionally for the presence of vaginal *Ureaplasma urealyticum* (one of seven species of *Ureaplasma*) at 38 weeks of pregnancy using a commercially available kit. Tests are performed with a Duplic$\alpha^{RealTime}$ *Ureaplasma urealyticum* detection kit (commercially available from EuroClone S.P.A., Pero, Italy). Only ten tests indicate the positive presence of *Ureaplasma urealyticum*. Twenty devices as described in Example 1 are distributed to the same twenty women at 39.5 weeks of pregnancy. Each woman self-collects a sample of vaginal fluid with a flocked swab and places the entire swab into the incubator. The incubators are sealed closed and placed with twenty environmental chambers each of which is maintained at 37° C. for the final week of the pregnancy. At the end of 40 weeks, each woman delivered a healthy infant and the incubators were checked for the presence of *Ureaplasma urealyticum*. Of the ten women who tested positive for *ureaplasma* in the conventional test, only five showed the presence of *Ureaplasma urealyticum* in their respective incubators. Of the ten women who tested negative for *Ureaplasma urealyticum* in the conventional test, one showed the positive presence of *Ureaplasma urealyticum* in the incubator. These results indicate that when women are tested for the presence of *Ureaplasma urealyticum* closer to the actual date of delivery using the devices and methods of the invention, false positives can be eliminated and false negatives identified. This allows for the administration of antibiotics to individuals who would otherwise not receive treatment due to false negatives and avoid excess treatment to individuals who otherwise show false positives or otherwise resolve an *Ureaplasma urealyticum* infection prior to delivery.

Example 3

FIGS. 2A-D depict views of another embodiment of an incubator 200. Preferably, incubator 200 is a cylinder, however incubator 200 can have another shape, such as a cube, a pyramid, or a sphere. Incubator 200 can be made of plastic, metal, glass, or another manmade or naturally occurring material. Preferably, the material is non-reactive to any fluids contained within incubator 200. Preferably, incubator 200 has a body 205 and a lid 210. Body 205 preferably has flat bottom surface 215 so that incubator 200 can be placed upright on a table or other surface. Lid 210 preferably can be secured within body 205. Preferably, lid 210 is screwed into body 205, however lid 210 can be snapped into body 205, friction fitted into body 205 or secured in another method. In a preferred embodiment lid 210 can be secured to and removed from body 205 multiple times. In other embodiments, lid 210 can only be secured to body 205 once and then is permanently fixed to body 205.

Preferably a threaded insert 218 is fixed within body 205. Threaded insert 218 is preferably coupled to body 205 with adhesive, however other fasteners can be used. For example, threaded insert 218 can be coupled to body 205 with a threaded engagement, friction, cotter rings, or other fastening devices. Preferably, a threaded portion of lid 210 engages a threated portion of threaded insert 218. Once engaged, incubator 200 is preferably air and/or water tight. Preferably, no gases or liquids can enter or escape from incubator 200 once it is closed. Preferably, incubator 200 is hermetically sealed. In order to achieve proper sealing, washers, gels, or other sealants may be placed between and/or around threaded insert 218 and lid 210.

Preferably, a swab 220 is integrated into lid 210. Swab 220 is preferably comprised of a rod having a first end attached to lid 210 and a second end attached to a sample obtaining device. Preferably, the sample obtaining device is cotton, another fabric, an adhesive, a magnet, a grabber, or another device capable of maintaining contact with a sample. Preferably, the rod is solid. The rod may be flexible or in-flexible. Preferably, incubator 200 has a multi-chamber core 225, a portion of which swab 220 can be inserted into. Preferably the upper chamber 225 of core 225 is an open space into which swab 220 can be inserted without encountering any fluids. Prior to use, swab 220 may be store in the upper chamber 225 to prevent contamination of swab 220. In such embodiments, lid 210 may have a pre-use and post-use engagement setting. For example, pre-use or prior to obtaining a sample, lid 210 may only partially be coupled to body 205 and post-use or after obtaining a sample, lid 210 may fully engage body 205.

Preferably, incubator 200 also has a middle chamber 230. Middle chamber 230 preferably contains the culture medium, sample preserver, or other fluid. Preferably middle chamber 230 is separated from upper chamber 225 by a penetrable membrane 235. Preferably, penetrable membrane 235 keeps the culture medium from escaping into the upper chamber prior to swab 220 coming into contact with the culture medium. For example, as swab 220 (after obtaining the sample) is inserted into core, the tip of swab 220 is forced through penetrable membrane 235 so that the culture medium is allowed to come into contact with the sample. Penetrable membrane 235 may rip, be pushed out of the way, dissolve, open, retract, or otherwise allow swab 220 into middle chamber 230. Middle chamber 230 may be refillable or be for onetime use. Additionally, if middle chamber 230 is refillable, penetrable membrane 235 may be resettable or replaceable. Furthermore, there may be multiple middle chambers 230 each filled with similar or different fluids. For example, a first middle chamber may be filled with a first substance and a second middle chamber may be filled with a second substance that when combined produce a chemical reaction that is necessary in analyzing the sample.

Preferably, incubator 200 also has a lower chamber 240. Preferably, lower chamber 240 contains conditioning electronics 245. Preferably, lower chamber is protected from ingress of fluids from either upper chamber 225 or middle chamber 235 by seal 260. Lower chamber 240 may contain a battery 250 or other power source, an activation switch, and a fluid agitation device. For example, the fluid agitation device may be a vibrating device, a pump, a propeller, or another device capable of moving fluids. In the case of a pump or a propeller, preferably a portion of the device is in contact with the fluids and a portion is maintained as separate from the fluids. The fluid agitation device may work continuously or intermittently. The incubator may additionally include a micro-fluidic device. The micro-fluidic device may allow for the inclusion of a lateral flow assay/device to be incorporated into the incubator for testing the sample when incubation is complete with or without an incorporated optical reader.

In other embodiments the fluid agitation device may be replaced or accompanied by another device. For example, the incubator 200 may include a heating or cooling device, drying device, a wetting device, an aerating, or another fluid conditioning device. Preferably, the electronics only activate upon the swab 220 entering the middle chamber 230. For example, as swab 220 is forced into the middle chamber 230, the swab contacts a bottom surface of middle chamber 230 which engages the switch 255 within lower chamber 240 and activates the vibration device. Switch may also be a pressure, volume, optical or electronic trigger. Preferably, the battery is replaceable for multiple uses, however incubator 200 may be a onetime use device. Incubator 200 may be a standalone device or may be used in conjunction with a heating element and/or processor as described herein.

Example 4

Figure 3:
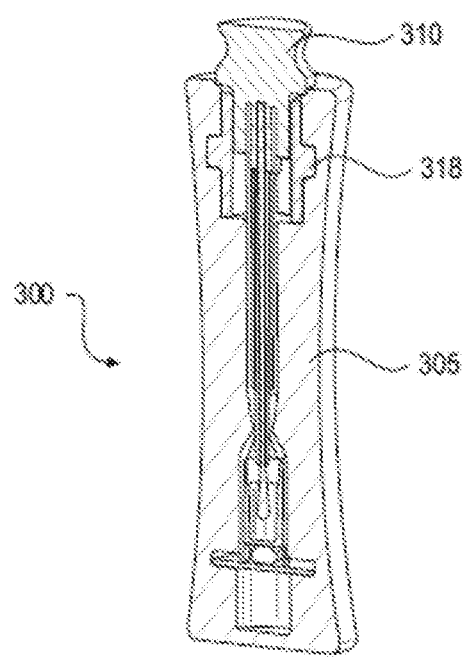
FIG. 3 Another embodiment of an incubator of the invention.

FIG. 3 depicts another example of an incubator 300. Incubator 300 is similar to incubator 200, except the lid 310 of incubator 300 is a stopper. Preferably lid 310 is friction fitted into an insert 318 that is coupled to the body 305 of incubator 300. Insert 318 preferably is made of a substance that increases the friction between lid 310 and body 305. For example, insert 320 may be rubber, a knurled surface, adhesive, or another material with a high coefficient of friction.

Example 5

Figure 4:
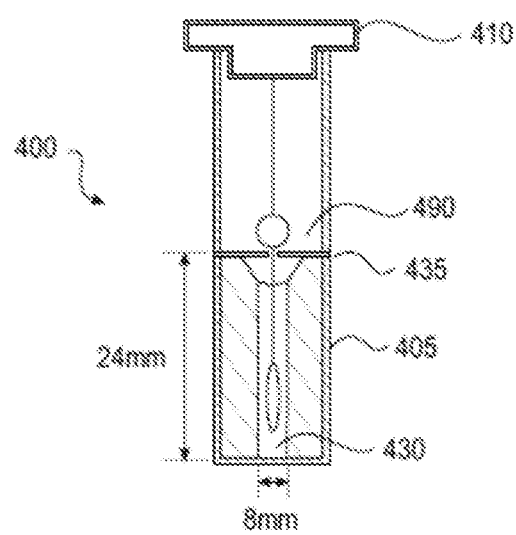
FIG. 4 Another embodiment of an incubator of the invention.

FIG. 4 depicts another example of an incubator 400. Incubator 400 is similar to incubator 200, except incubator 400 includes a ball seal 490 coupled to swab 420. Preferably, ball seal 490 provides a secondary seal to penetrable membrane 435. For example, after swab 420 pierces penetrable membrane 435, ball seal 490 engages the hole in penetrable membrane 435 to limit the fluid from exiting the middle chamber. Additionally, ball seal 490 may provide a limit to how far into the middle chamber swab 420 can extend. Ball seal 490 is preferably made of rubber, but other materials can be used.

Example 6

Figure 5:
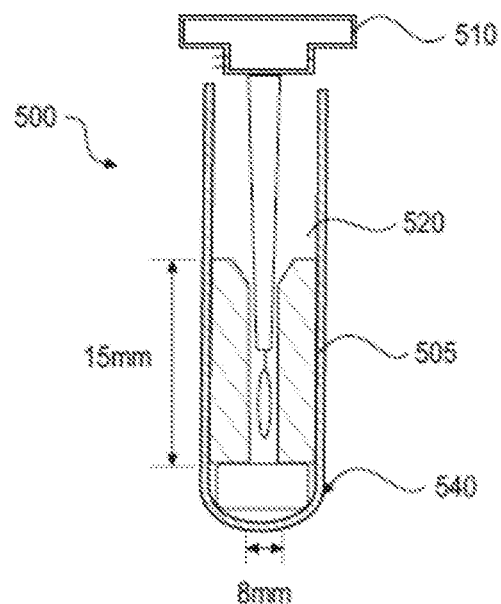
FIG. 5 Another embodiment of an incubator of the invention.

FIG. 5 depicts another example of an incubator 500. Incubator 500 is similar to incubator 200, except the rod of swab 520 is tapered. Preferably, the tapered rod provides a secondary seal to penetrable membrane 535. For example, after swab 520 pierces penetrable membrane 535, the tapered rod engages the hole in penetrable membrane 535 to limit the fluid from exiting the middle chamber. Additionally, the tapered rod may provide a limit to how far into the middle chamber swab 520 can extend. The tapered rod is preferably made of rubber, but other materials can be used.

Example 7

Figure 6:
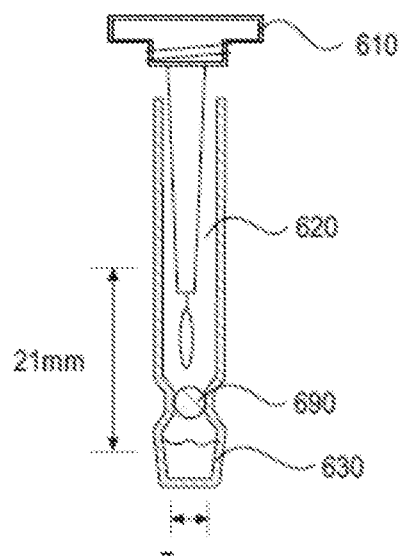
FIG. 6 Another embodiment of an incubator of the invention.

FIG. 6 depicts another example of an incubator 600. Incubator 600 combines the tapered rod of incubator 500 with the ball seal of incubator 400. In incubator 600, ball seal 690 replaces the penetrable membrane of incubator 200. For example, ball seal 690 preferably contains the fluid in the middle chamber until swab 620 forces ball seal 690 into the middle chamber or aside, at which point the fluid within the middle chamber can come into contact with the sample. Then, the tapered rod engages the hole left by ball seal 690 or with ball seal 690 to limit the fluid from exiting the middle chamber. Additionally, the tapered rod may provide a limit to how far into the middle chamber swab 620 can extend. The tapered rod and ball seal 690 are preferably made of rubber, but other materials can be used.

Example 8

Figure 7B:
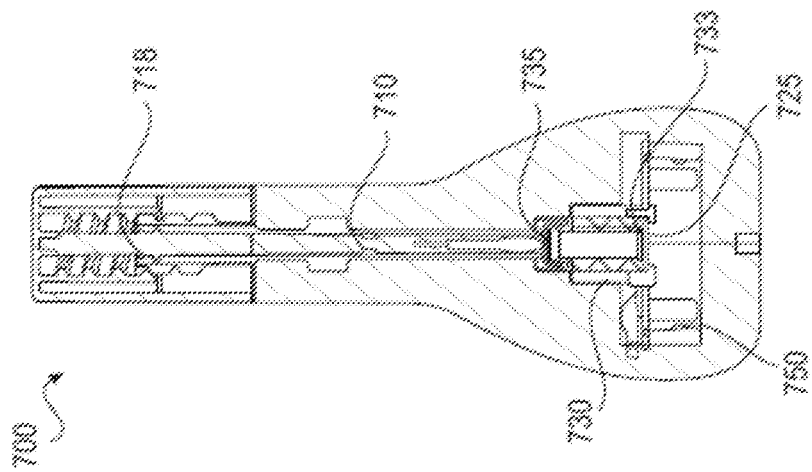
FIGS. 7A-B Views of another embodiment of an incubator of the invention.
Figure 7A:
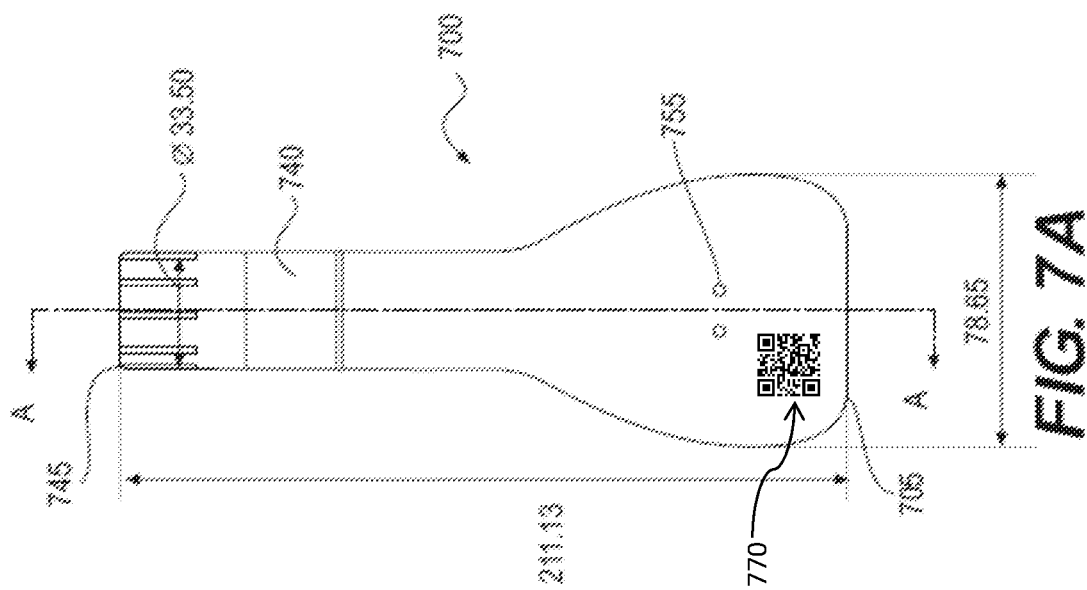

FIGS. 7A and 7B depict an exterior and cross-sectional views of another embodiment of an incubator 700. Preferably, incubator 700 has a teardrop shape, however incubator 700 can have another shape, such as a cube, a pyramid, a cylinder, or a sphere. Incubator 700 can be made of plastic, metal, glass, or another manmade or naturally occurring material. Preferably, the material is non-reactive to any fluids contained within incubator 700. Preferably, incubator 700 has a body 705 and a sample assembly 710. Sample assembly 710 preferably can be secured within body 705. Preferably, body 705 surrounds sample assembly 710 however sample assembly 710 can be screwed into body 705, snapped into body 705, friction fitted into body 705 or secured in another method. In a preferred embodiment sample assembly 710 can be secured to and removed from body 705 multiple times. In other embodiments, sample assembly 710 can only be secured to body 705 once and then is permanently fixed to body 705.

Sample assembly 710 is preferably air and/or water tight. Preferably, no gases or liquids can enter or escape from sample assembly 710 once it is secured. Sample assembly 710 is hermetically sealed. In order to achieve proper sealing, washers, gels, or other sealants be positioned within sample assembly 710.

Figure 8B:
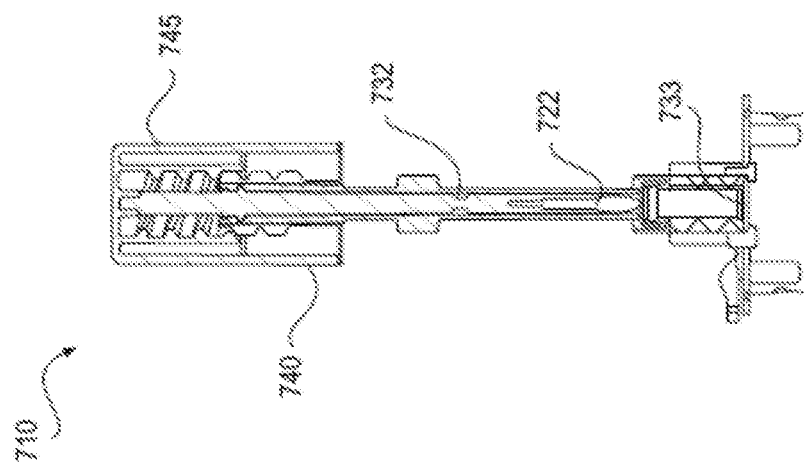
FIGS. 8A-B Views of an embodiment of a swab of the invention.
Figure 8A:
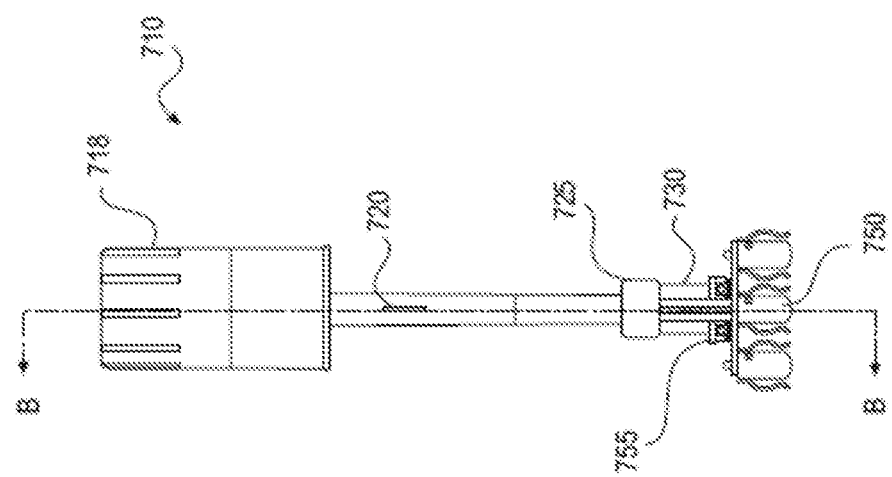
Figure 9A:
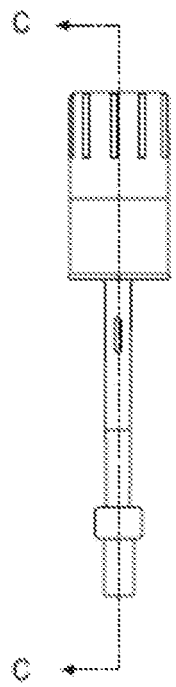
FIGS. 9A-C Views of an embodiment of the swab prior to penetrating the ampule.
Figure 9B:
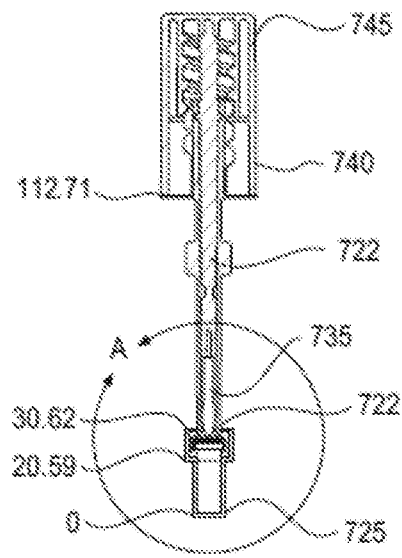
Figure 9C:
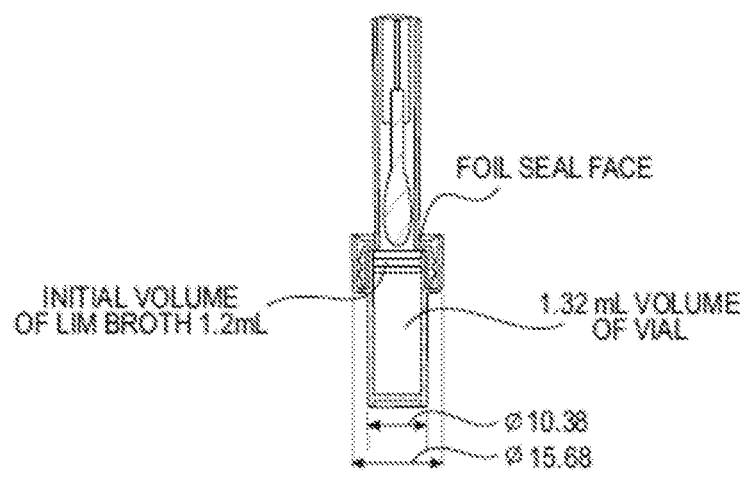
Figure 10A:
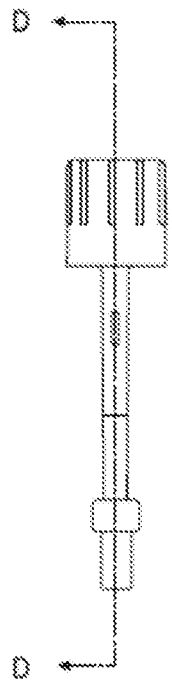
FIGS. 10A-C Views of an embodiment of the swab after penetrating the ampule.
Figure 10B:
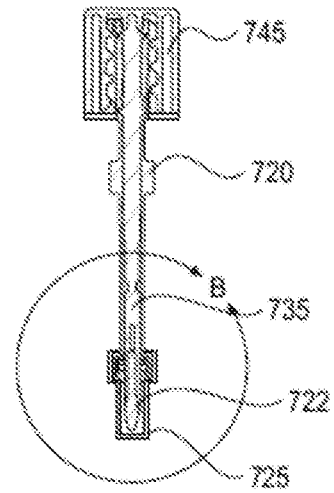
Figure 10C:
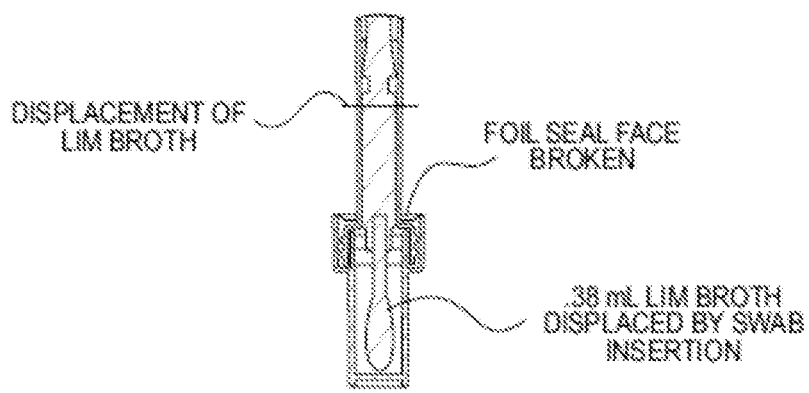

FIGS. 8A and 8B depict an exterior and cross-sectional views of an embodiment of sample assembly 710. Sample assembly preferably comprises a lid 718, a tube 720 containing a swab 722, and an ampule 725. Swab 722 is preferably removable from tube 720 for obtaining a biological sample. Preferably, swab 722 is cotton, another fabric, an adhesive, a magnet, a grabber, or another device capable of maintaining contact with a sample. Preferably, swab 722 is coupled to lid 718 by a rod 732. The rod 732 may be flexible or in-flexible. Prior to use, swab 722 may be stored in the tube 720 to prevent contamination of swab 722. In such embodiments, lid 718 may have a pre-use and post-use engagement setting. For example, pre-use or prior to obtaining a sample, lid 718 be in a sample collecting position (see FIGS. 9A-C) and after obtaining a sample, lid 718 may be forced into a sample incubating position (see FIGS. 10A-C). Prior to use, lid 718 preferably has a tamper evident device to indicate if the assembly 710 has been opened, thereby alerting a user that the assembly may be compromised and should be discarded. For example, lid 718 may have a breakaway section that remains attached to assembly 710 when lid 718 is first removed from assembly 710 or otherwise indicates that lid 708 has been removed from assembly 710. Preferably, in the sample incubating position, swab 722 is forced into ampule 725 so that the biological sample may come into contact with a material contained within ampule 725. For example, lid 718 may be comprised of a fixed portion 740 and a rotating portion 745. By unscrewing rotating portion 745, swab 722 may be removed from sample assembly 710. After collecting the sample, rotating portion 745 may be screwed back into fixed portion 740 past the sample collecting position into the sample incubating position.

Ampule 725 may have a penetrable membrane 735. Preferably, penetrable membrane 735 keeps the culture medium from escaping into the tube 720 prior to swab 722 coming into contact with the culture medium. For example, as swab 722 (after obtaining the sample) is inserted back into tube 720, the tip of swab 722 is forced through penetrable membrane 735 so that the culture medium is allowed to come into contact with the sample. Penetrable membrane 735 may rip, be pushed out of the way, dissolve, open, retract, or otherwise allow swab 722 into ampule 725. Ampule 725 may be refillable or be for onetime use. Additionally, if ampule 725 is refillable, penetrable membrane 735 may be resettable or replaceable. Furthermore, there may be multiple ampules 725 each filled with similar or different fluids. For example, a first ampule may be filled with a first substance and a second ampule may be filled with a second substance that when combined produce a chemical reaction that is necessary in analyzing the sample.

Figure 11:
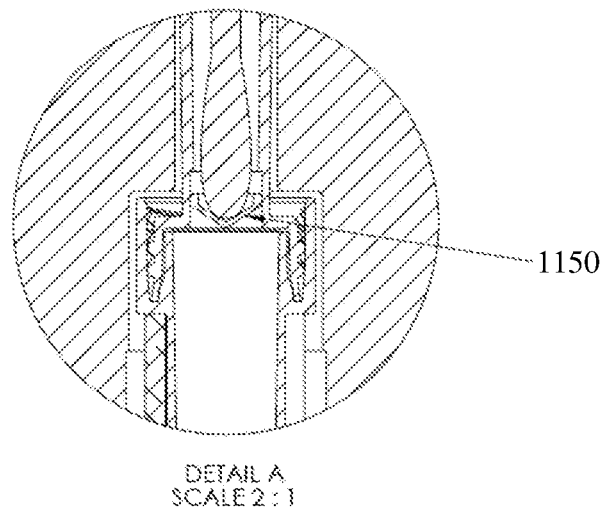
FIG. 11 View of another embodiment of an incubator of the invention.

Additionally, as shown in FIG. 11, a seal piercing device 1150 may be positioned between the swab and the penetrable membrane. Preferably, the piercing device 1150 is conical in shape with a pointed tip positioned adjacent to the penetrable membrane. However, the piercing device 1150 can have another shape, such as a "V" shape, or have a sharp edge. Preferably piercing device 1150 facilitates the entry of the swab through the penetrable membrane. Additionally, piercing device 1150 may prevent a sample on the swab from being rubbed off or squeezed out during entry of the swab into the ampule. After the sample is obtained and the swab is screwed into the device, piercing device 1150 is pushed by the swab through the penetrable membrane and into the ampule. Piercing device 1150 may be comprised of a variety of materials. Piercing device 1150 can contain, be coated with, or be made of a variety of chemicals, compounds, elements, drugs, etc. that could enhance identification or growth of the desired organism(s) or otherwise assist in evaluating the sample.

Preferably, sample assembly 710 also has a conditioning element 730. Preferably, conditioning element 730 is protected from ingress of fluids and contains a battery 750. Preferably, conditioning element 730 is a heating or cooling device, drying device, a wetting device, an aerating, a fluid agitation device, or a combination thereof. For example, the fluid agitation device may be a vibrating device, a pump, a propeller, or another device capable of moving fluids. In the case of a pump or a propeller, preferably a portion of the device is in contact with the fluids and a portion is maintained as separate from the fluids. The fluid agitation device may work continuously or intermittently. The incubator may additionally include a micro-fluidic device. The micro-fluidic device may allow for the inclusion of a lateral flow assay/device to be incorporated into the incubator for testing the sample when incubation is complete with or without an incorporated optical reader. In other embodiments, conditioning element 730 may be a mobile genetic element that contains a gene and a recombination site. For example, a PCR or mold cassette. The cassette is preferably insertable into and removable from sample assembly 710. The cassette may be adapted to be coupled to sample assembly 710's power source. In other embodiments, the cassette may be built-in and non-removable. The results from the testing may be read by an optical reader within the assembly 710 or another reader capable of determining the results of the test. Preferably the cassette is coupled to ampule 725 vile by micro-fluidics.

Preferably, conditioning element 730 only activate upon the swab 722 entering the ampule 725. For example, as swab 722 is forced into ampule 725, the swab contacts a bottom surface of ampule 725 which engages a switch 733 of conditioning element 730 and activates device. The switch may also be a pressure sensor, a volume sensor, an optical reader adapted to detect the presence of the swab or sample, or an electronic trigger. Preferably, the battery is replaceable for multiple uses, however incubator 700 may be a onetime use device. Incubator 700 may be a standalone device or may be used in conjunction with an external heating element and/or processor as described herein. Incubator 700 may have one or more lights 755 or indicators to indicate the current status of the incubator.

Other embodiments and uses of the invention will be apparent to those skilled in the art from consideration of the specification and practice of the invention disclosed herein. All references cited herein, including all publications, and all U.S. and foreign patents and patent applications are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A portable incubator, comprising:
   a hand-held base;
   a sample assembly contained within the hand-held base;
   a power source contained within the hand-held base; and
   a diagnostic device contained within the hand-held base and powered by the power source;
   wherein, the sample assembly comprises:
      a lid removably coupled to and extending above a top of the hand-held base;
      a sample gathering device coupled to the lid;
      a tube adapted to mate with the lid and house the sample gathering device;
      an ampule coupled to the tube and having a seal;
      a seal piercing device positioned within the tube and above the seal adapted to pierce the seal; and
      a sample conditioning device;
      wherein the sample assembly is positionable between a sample gathering position and
      a sample incubating position.

2. The incubator of claim 1, wherein the sample gathering device is a flocked swab.

3. The incubator of claim 2, wherein the flocked swab is coupled to the lid by a rod.

4. The incubator of claim 1, wherein the sample conditioning device is an electrically powered sample conditioning device.

5. The incubator of claim 1, wherein the sample conditioning device is one of a fluid agitator or a micro-fluidic device.

6. The incubator of claim 1, further comprising a switch adapted to activate the sample conditioning device.

7. The incubator of claim 1, wherein the sample gathering device and the seal piercing device are maintained outside the ampule in the sample gathering position and are forced into the ampule in the sample incubating position.

8. The incubator of claim 1, wherein the seal is a penetrable membrane separating contents of the ampule from the sample gathering device.

9. The incubator of claim 1, wherein the incubator is adapted to collect, process, transport, and stabilize a sample for use in biomarker determinations or cancer tissue testing.

10. The incubator of claim 1, wherein the incubator is adapted to collect, incubate, and transport a biological sample.

11. The incubator of claim 1, wherein the seal piercing device contains a chemical, a compound, an element, or a drug adapted to promote identification, evaluation, or growth of a sample; is coated with a compound, an element, or a drug adapted to promote identification, evaluation, or growth of a sample; or is made of a compound, an element, or a drug adapted to promote identification, evaluation, or growth of a sample.

12. The incubator of claim 1, wherein the diagnostic device is one of an insertable and removable cassette or a non-removable cassette.

13. The incubator of claim 12, wherein the incubator and cassette are single use and disposable.

14. The incubator of claim 1, further comprising a communication device coupled to the incubator adapted to communicate with an external computing device.

15. The incubator of claim 14, wherein the communication device is a scannable indicator adapted to provide information about the incubator to the external computing device.

16. A sample evaluation system, comprising:
   a portable incubator comprising:
      a hand-held base;
      a sample assembly contained within the hand-held base;
      a power source contained within the hand-held base; and
      a diagnostic device contained within the hand-held base and powered by the power source;
      wherein, the sample assembly comprises:
         a lid removably coupled to and extending above a top of the hand-held base;
         a sample gathering device coupled to the lid;
         a tube adapted to mate with the lid and house the sample gathering device;
         an ampule coupled to the tube and having a seal;
         a seal piercing device positioned within the tube and above the seal adapted to pierce the seal; and
         a sample conditioning device;
         wherein the sample assembly is positionable between a sample gathering position and a sample incubating position; and
      a sample conditioning medium housed within the ampule.

17. The system of claim 16, wherein the sample gathering device is a flocked swab.

18. The system of claim 16, wherein the flocked swab is coupled to the lid by a rod.

19. The system of claim 16, wherein the sample conditioning device is an electrically powered sample conditioning device.

20. The system of claim 16, wherein the sample conditioning device is one of a fluid agitator or a micro-fluidic device.

21. The system of claim 16, further comprising a switch adapted to activate the sample conditioning device.

22. The system of claim 16, wherein the sample gathering device is maintained outside the ampule in the sample gathering position and is forced into the ampule in the sample incubating position.

23. The system of claim 16, wherein the seal is a penetrable membrane separating contents of the ampule from the sample gathering device.

24. The system of claim 16, wherein the sample is a microorganism or group of microorganisms and the sample conditioning fluid is a culture medium that promotes the proliferation or stabilization of the microorganism or group of microorganisms.

25. The system of claim 16, wherein the incubator is adapted to collect, process, transport, and stabilize the sample for use in biomarker determinations or cancer tissue testing.

26. The system of claim 16, wherein the seal piercing device contains a chemical, a compound, an element, or a drug adapted to promote identification, evaluation, or growth of a sample; is coated with a compound, an element, or a drug adapted to promote identification, evaluation, or growth of a sample; or is made of a compound, an element, or a drug adapted to promote identification, evaluation, or growth of a sample.

27. The system of claim 16, wherein the diagnostic device is one of an insertable and removable cassette or a non-removable cassette.

28. The system of claim 27, wherein the incubator and cassette are single use and disposable.

29. The system of claim 16, further comprising an external computing device and a communication device coupled to the incubator adapted to communicate with the external computing device.

30. The system of claim 29, wherein the communication device is a scannable indicator adapted to provide information about the incubator to the external computing device or a wired.

* * * * *